US00PP35014P2

(12) United States Plant Patent
Bedard

(10) Patent No.: US PP35,014 P2
(45) Date of Patent: Mar. 7, 2023

(54) GRANDIFLORA ROSE PLANT NAMED 'WEKGOAGRORO'

(50) Latin Name: *Rosa hybrida*
Varietal Denomination: WEKgoagroro

(71) Applicant: Early Morning LLC, Lawrenceburg, IN (US)

(72) Inventor: Christian Bedard, Rancho Cucamonga, CA (US)

(73) Assignee: Early Morning LLC, Lawrenceburg, IN (US)

( * ) Notice: Subject to any disclaimer, the term of this patent is extended or adjusted under 35 U.S.C. 154(b) by 0 days.

(21) Appl. No.: 17/863,765

(22) Filed: Jul. 13, 2022

Related U.S. Application Data

(63) Continuation of application No. 17/300,839, filed on Nov. 22, 2021.

(51) Int. Cl.
*A01H 5/02* (2018.01)
*A01H 6/74* (2018.01)

(52) U.S. Cl.
USPC ..... Plt./132
CPC ..... *A01H 6/749* (2018.05)

(58) Field of Classification Search
USPC ..... Plt./132
CPC ..... A01H 6/749
See application file for complete search history.

(56) References Cited

U.S. PATENT DOCUMENTS

PP13,089 P3 10/2002 Zary
PP20,936 P2 4/2010 Carruth
PP26,052 P3 11/2015 Carruth

OTHER PUBLICATIONS

CPVO hit on Grandiflora rose plant named 'WEKGoagroro', QZ PBR 20221871, filed Aug. 9, 2022.*
Prior Product Sales, 1 page, Jan. 15, 2021.
Prior Product Sales, 1 page, Mar. 8, 2021.
Rose (Rosa 'Dr. Huey') in the Roses Database, Garden.org, https://garden.org/plants/view/1545/Rose-Rosa-Dr-Huey/ (last visited Dec. 15, 2021), 9 pages.
Weeks Roses Wholesale Rose Catalog, "Pop Art," 13 pages, 2022.

* cited by examiner

*Primary Examiner* — Anne Marie Grunberg
(74) *Attorney, Agent, or Firm* — McKee, Voorhees & Sease, PLC

(57) ABSTRACT

A new variety of Grandiflora rose plant suitable for garden decoration, having flowers of pink & yellow striped coloration.

1 Drawing Sheet

Classification: The present invention relates to a new *Rosa hybrida* plant.

Variety denomination: The new plant has the varietal denomination 'WEKgoagroro'.

BACKGROUND OF THE INVENTION

This invention relates to a new and distinct variety of Grandiflora Rose. It has as its seed parent the variety known as 'WEKgobafa' (U.S. Plant Pat. No. 26,052) and as its pollen parent the variety known as 'WEKgobnez' (U.S. Plant Pat. No. 20,936).

SUMMARY OF THE INVENTION

Among the features which distinguish the new variety from other presently available and commercial rose cultivars known to the inventor are the following combinations of characteristics: its unique pink & yellow striped flower coloration, its strong fruity to citrus-like fragrance, its excellent color stability throughout the life of the flower and its yellow-green stigmas. The plant has an upright, bushy somewhat spreading growing habit, suitable for outdoor garden decoration.

Asexual reproduction of the new variety by budding as performed in Kern County, Calif., shows that the foregoing and other distinguishing characteristics come true to form and are established and transmitted through succeeding asexual propagations. 'WEKgoagroro' may be asexually propagated by cuttings, budding and grafting. The budding and grafting successfully occurred on the plant/rootstock *Rosa hybrida* cv. 'Dr. Huey' (not patented).

Comparison With Parents

The new rose may be distinguished from its seed parent, 'WEKgobafa' by the following combination of characteristics: whereas 'WEKgoagroro' bears very double flowers (about 52 to 75 petals) of pink & yellow striped coloration, 'WEKgobafa' bears double flowers of deep golden orange coloration finished with a kiss of red with significantly lesser petalage (about 27 to 35 petals). The new variety has a strong fruity to citrus-like fragrance, whereas the seed parent has a slight fruity to somewhat tea fragrance.

The new variety may be distinguished from its pollen parent, 'WEKgobnez' by the following combination of characteristics: whereas 'WEKgoagroro' bears very double flowers (about 52 to 75 petals) of pink & yellow striped coloration, 'WEKgobafa' bears very double flowers of burgundy and cream striped bicolor coloration with lesser petalage (about 41 to 66 petals). The new variety has an upright, bushy somewhat spreading medium height growing habit (about 82 to about 130 cm. in height), whereas the pollen parent has an upright moderately spreading significantly taller growing habit (about 140 to about 165 cm. in height).

Comparison With the Closest Commercially Available Cultivar

The new variety may be distinguished from its closest commercially available cultivar, 'JACepirt' (U.S. Plant Pat. No. 13,089) by the following combination of characteristics: whereas 'WEKgoagroro' bears very double flowers (about 52 to 75 petals) with a strong fruity to citrus-like fragrance, 'JACepirt' bears double flowers with a moderate spicy fragrance and with significantly lesser petalage (about 25 petals). The new variety has an upright, bushy somewhat spreading medium height growing habit (about 82 to about 130 cm. in height), whereas the closest commercially available cultivar has a vigorous upright significantly taller growing habit (about 170 cm. in height).

BRIEF DESCRIPTION OF ILLUSTRATION

The accompanying photograph illustrates the new variety and shows the flowering thereof from bud to full bloom depicted in color as nearly correct as it is possible to make in a color illustration of the character. The branches used for the photograph came from 3 to 4 year-old rose plants of the new variety grown outdoors in Wasco, Calif. in the month of November. Throughout this specification, color references and/or values are based upon The Colour Chart of The Royal Horticultural Society (1966) except where common terms of color definition are employed.

DESCRIPTION OF THE NEW VARIETY

The following description is of 3 to 4 year-old rose plants of the new variety grown outdoors in Rancho Cucamonga, Calif. in the month of November. Phenotypic expression may vary with environmental, cultural and climatic conditions, as well as differences in conditions of light and soil.

FLOWER

The new variety usually bears its flowers singly. Flowers are borne on strong somewhat short to medium length stems (about 15 to about 66 cm.). Outdoors, the plant blooms abundantly and nearly continuously during the growing season. The flowers have a strong fruity to citrus-like fragrance.

BUD

The peduncle is about 2.1 to about 5.0 cm. in length, of average caliper (about 0.3 to about 0.4 cm. in diameter), and usually erect. It is moderately rough, with some stipitate glands, very few hairs and few small prickles. Peduncle color is between 146C and 146A often lightly suffused, especially on the side exposed to the sun, with between 187C and 187B.

Before the calyx breaks, the bud is about 1.2 to about 2.0 cm. in diameter at the widest point, about 1.2 to about 1.9 cm. in length, and moderately ovoid to somewhat globular in shape. The surface of the bud bears between 6 to 8 foliaceous appendages, few stipitate glands and some hairs, usually with slender entire foliaceous parts extending beyond the tip of the bud about ¾ or more of its length. Bud color is between 137C and 146A sometimes moderately suffused, especially on the side exposed to the sun, with between 187A and 187B.

The sepals are 5 per flower, about 2.1 to about 3.7 cm. in length and about 0.6 to about 1.1 cm. in width at the widest point. The outer surface color of the sepal is between 137C and 146A sometimes moderately suffused, especially on the side exposed to the sun, with between 187A and 187B. The outer surface of the sepal is somewhat rough and bears between 0 to 3 foliaceous appendages with few stipitate glands, and some hairs. The inner surface color of the sepal is near 146C broadly bordered by near 137B. After the sepals open, the inner surface color is sometimes heavily suffused, especially on the area exposed to the sun, with between 187A and 187B. The inner surface of the sepal is covered with fine wooly tomentum; sepal margins are entire and lined with some stipitate glands and hairs. The sepals are moderately permanent, and usually straight in shape with acute apices.

The receptacle of the flower is of somewhat short to medium length (about 0.4 to about 0.7 cm.) and moderately thin to average in caliper (about 0.7 to about 1.1 cm. in diameter). The receptacle is urn-shaped in form. Its surface is smooth with few hairs and with somewhat thin fleshy walls. The receptacle color is between 144A and 146A sometimes moderately suffused, especially on the side exposed to the sun, with between 187C and 187B.

As the petals open (after the calyx breaks), the bud is about 1.8 to about 2.6 cm. in diameter at the widest point, about 1.9 to about 2.9 cm. in length, and ovoid to somewhat pointed in form. The color of the under surfaces of the newly opened petals is between 20C and 19C often heavily suffused with between 60A and 53A to as dark as between 187A and 187B. At the point where the petal attaches, there is a large zone of between 10A and 7D. The color of the upper surfaces of the newly opened petals is irregularly striped and flecked with as dark as between 63A and 59D, to as light as between 4B and 3C. At the point where the petal attaches, there is a large zone of between 5C and 4A.

BLOOM

When fully open, the bloom ranges from about 7.5 to about 11.2 cm. in diameter. Petalage is very double with about 52 to 75 petals and about 4 to 17 petaloids irregularly arranged. When partially open, the bloom form is somewhat globular to moderately cupped, and the petals are moderately tightly spiraled to cupped to somewhat undulated with petal edges somewhat reflexed outward. When fully open, the bloom form is cupped, and the petals are loosely cupped to somewhat undulated with petal edges somewhat reflexed outward.

PETALS

The substance of the petals is moderately heavy and of medium to somewhat thick thickness, with upper surfaces slightly satiny and under surfaces moderately shiny. The petals are about 3.0 to about 5.7 cm. in length and about 1.9 to about 5.6 cm. in width at the widest point. The petals reflex one by one. Petal margins are entire.

The outer petals are somewhat obovate to nearly rounded in shape with rounded apices.

The inner petals are obovate in shape with rounded apices.

Petaloids are about 0.6 to about 3.1 cm. in length and about 0.3 to about 2.3 cm. in width at the widest point.

Petaloids are irregularly shaped moderately obovate to somewhat oblanceolate to subulate with rounded apices sometimes slightly notched with one to two notches.

NEWLY OPENED FLOWER

The under surface color of the outer, intermediate and inner petals is between 3D and 8D. There is no visible change in coloration at the point where the petal attaches. The upper surface color of the outer, intermediate and inner petals is irregularly striped and flecked with as dark as between 57D and 55A to as light as between 3D and 8D. At the point where the petal attaches, there is a very large zone of between 4B and 3C.

The under and upper surface colors of the petaloids are similar in coloration to the upper and under surfaces of the intermediate and inner petals.

The general tonality of the newly opened flower is irregularly striped and flecked with as dark as between 57D and 55A to as light as between 3D and 8D.

THREE-DAY-OLD FLOWER

The under surface color of the outer, intermediate and inner petals is between 4D and 8D. There is no visible change in coloration at the point where the petal attaches. The upper surface color of the outer, intermediate and inner petals is irregularly striped and flecked with as dark as between 68C and 58C to as light as between 4D and 8D. At the point where the petal attaches, there is a very large zone of between 4D and 2D.

The under and upper surface colors of the petaloids are similar in coloration to the upper and under surfaces of the intermediate and inner petals.

The general tonality of the three-day-old flower is irregularly striped and flecked with as dark as between 68C and 58C to as light as between 4D and 8D.

On the spent bloom, the petals usually drop off cleanly.

In November in Rancho Cucamonga, Calif., blooms on the bush growing outdoors generally last about four to five days. Cut roses from plants grown outdoors and kept at normal indoor living temperatures generally last about four to five days.

MALE REPRODUCTIVE ORGANS

Stamens are few in number (average about 55) and are arranged regularly about the pistils; a few are mixed with petaloids. The filaments are of somewhat short to medium length (about 0.3 to about 0.9 cm.) most with anthers. Filaments are between 13C and 12B in color. The anthers are moderately small for the class and all open approximately at the same time. Anther color when immature is near 23B on the external part and near 11C on the internal part. Anther color at maturity is near 163A on the external part and near 200A on the internal part. Pollen is moderately sparse and between 19D and 18C in color.

FEMALE REPRODUCTIVE ORGANS

Pistils vary in number (average about 75). The styles are moderately even, average to somewhat long in length (about 0.5 to about 1.0 cm.), moderately thin in caliper, and loosely bunched. Stigma color is between 150B and 154A. Style color is between 150D and 154D. Ovaries are usually all enclosed in the calyx. The ovaries are of small size and between 159B and 159C in color.

Hips have not been observed on this variety when grown in Rancho Cucamonga, Calif.

FOLIAGE

The compound leaves are usually comprised of three to seven leaflets and are borne abundantly. The seven-leaflet leaves are about 9.2 to about 14.3 cm. in length and about 6.6 to about 10.7 cm. in width at the widest point, moderately leathery to somewhat crisp in texture on both sides, and glossy in finish on the upper side and semi-glossy in finish on the under side. The leaves have a pinnate venation pattern. The terminal leaflets are about 4.0 to about 6.8 cm. in length and about 2.4 to about 4.5 cm. in width at the widest point, shaped moderately ovate to somewhat oval with acute apices and rounded to somewhat acute bases. Their margins are usually simply senate.

The upper surface color of the mature leaf is between 139A and 147A. The under surface color of the mature leaf is between 146A and 147C. The under and upper colors of the leaf veins on the mature leaf are similar in coloration to the upper and under surfaces colors of the mature leaf. The upper surface color of the young leaf is between 137A and 146A, often heavily suffused with between 187A and 187B. The under surface color of the young leaf is between 146B and 146C, often heavily suffused with between 187B and 187C. The under and upper colors of the leaf veins on the young leaf are similar in coloration to the upper and under surfaces colors of the young leaf.

The rachis is about 3.9 to about 6.4 cm. in length, about 0.1 to about 0.2 cm in width at the widest point, and rough. The upper side is moderately deeply grooved with few hairs and some stipitate glands on the edges of the grooves. The under side of the rachis is rough with some hairs, few stipitate glands and few small prickles. The rachis color is near 146C on the under side and near 137B on the upper side, often heavily suffused on the young leaves with between 187B and 187A.

The stipules are about 1.0 to about 2.4 cm. in length and of medium width (about 0.4 to about 0.8 cm.) with long straight points that usually turn out at an angle of more than 45 degrees and sometimes recurve toward the stem. The under and upper surface color of the stipule is between 137A and 137B often moderately suffused on the young leaves with between 187B and 187A. The upper and under surfaces of the stipules are smooth in texture.

The petiole is average in caliper and rough. The upper side is moderately deeply grooved with few hairs and some stipitate glands on the edges of the grooves. The under side of the petiole is rough with some hairs, few stipitate glands and few small prickles. The petiole is about 0.4 to about 1.0 cm. in length and about 0.1 to about 0.2 cm in width at the widest point. The petiole color is near 146C on the under side and near 137B on the upper side, often heavily suffused on the young leaves with between 187B and 187A.

The plant displays an above average degree of resistance to powdery mildew (*Sphaerotheca pannosa*), downy mildew (*Peronospora sparsa*), and rust (*Phragmidium* sp.) as compared to other commercial varieties grown under comparable conditions in Rancho Cucamonga, Calif. The plant's winter hardiness and drought/heat tolerance are yet to be determined.

GROWTH

The plant has an upright, bushy somewhat spreading medium height growing habit (about 82 to about 130 cm. in height and about 76 to about 92 cm. spread at the widest point), with moderately full branching. It displays vigorous growth and the canes are of moderately light to medium sized caliper for the class (about 1.2 to about 2.2 cm. in diameter at the widest point).

The color of the major stems is between 137A and 137B. The major stems are rough in texture and they bear many large prickles that are about 0.5 to about 1.1 cm. in length. The large prickles are angled slightly downward with a medium length to somewhat long moderately narrow oval base; prickle color is between 200D and 165A. The major stem bears few small prickles of similar shape and coloration.

The color of the branches is between 146A and 147B. The branches are rough in texture and they some large prickles which are of similar shape to the large prickles on the major stems. The prickles are about 0.4 to about 0.7 cm. in length. Prickle color is near 152C usually heavily suffused with between 187C and 187B. The branches bear few small prickles of similar shape and coloration.

The color of the new shoots is between 146A and 147B often heavily suffused with between 187B and 187A. The new shoots are rough in texture and they bear some large prickles which are of similar size and shape to the large prickles on the branches; prickle color is near 152C usually heavily suffused with between 187C and 187B. The shoots bear few small prickles of similar shape and coloration.

I claim:

1. A new and distinct Grandiflora rose plant of the variety substantially as described and illustrated herein.

* * * * *

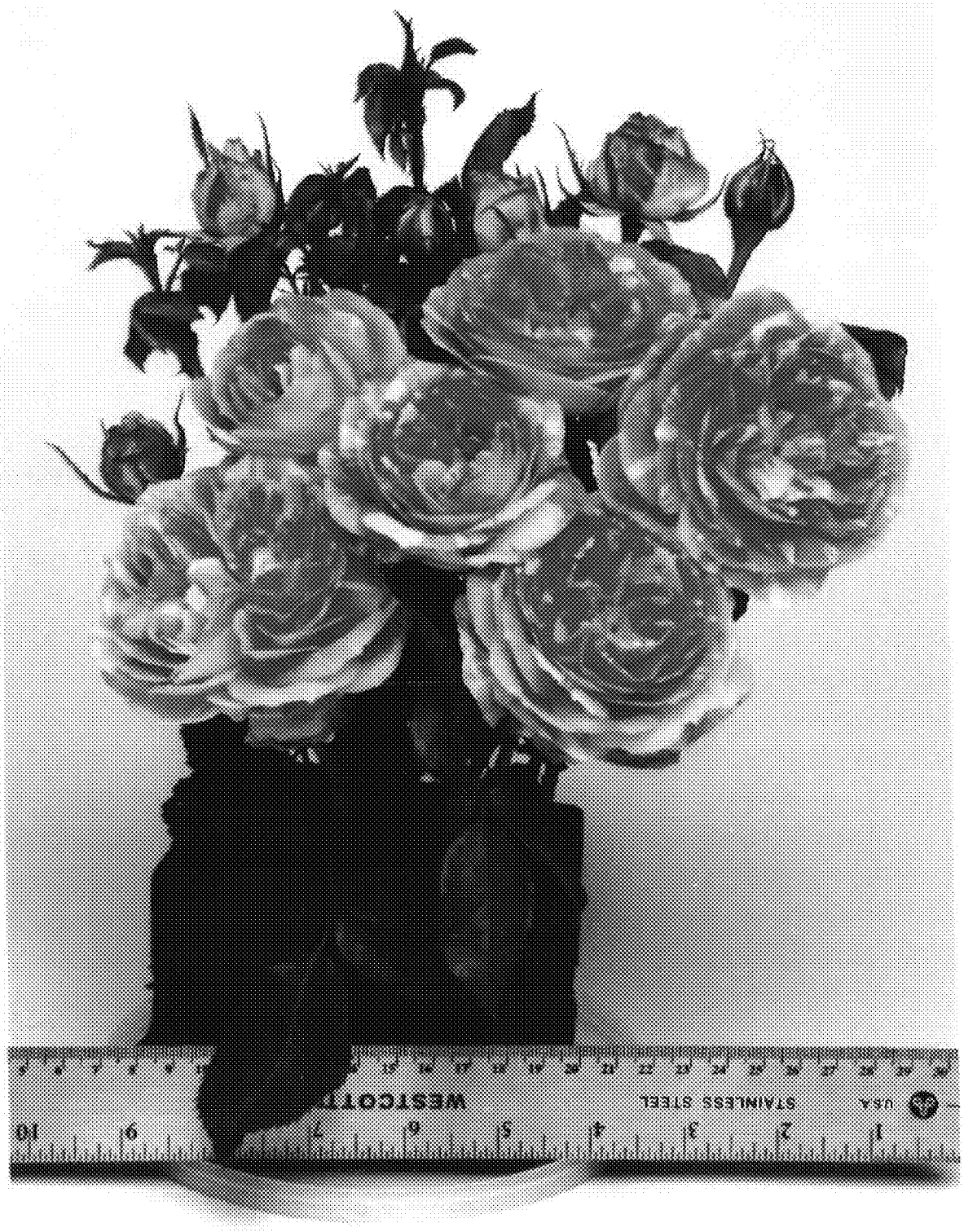
WESTCOTT
STAINLESS STEEL
USA